United States Patent [19]

Roberts et al.

[11] 4,080,831
[45] Mar. 28, 1978

[54] SECONDARY SAMPLING DEVICE

[75] Inventors: Hugh Hill Roberts; Gary R. West, both of Lakeland, Fla.

[73] Assignee: International Minerals & Chemical Corporation, Libertyville, Ill.

[21] Appl. No.: 791,914

[22] Filed: Apr. 28, 1977

[51] Int. Cl.² .......................... G01N 1/18; G01N 1/20
[52] U.S. Cl. .................................................. 73/421 A
[58] Field of Search .............. 73/421 A, 421 R, 422 R

[56] References Cited
U.S. PATENT DOCUMENTS

| 2,670,629 | 3/1954 | Belden ............................... 73/421 A |
| 3,942,388 | 3/1976 | Rathnow et al. .................. 73/421 A |

Primary Examiner—James J. Gill
Attorney, Agent, or Firm—Edward A. Figg; Howard E. Post

[57] ABSTRACT

A secondary sampling device for particulate matter is disclosed which includes a plurality of sample splitters arranged in series wherein each sample splitter is perpendicular to those adjacent thereto.

2 Claims, 4 Drawing Figures

U.S. Patent  March 28, 1978  4,080,831
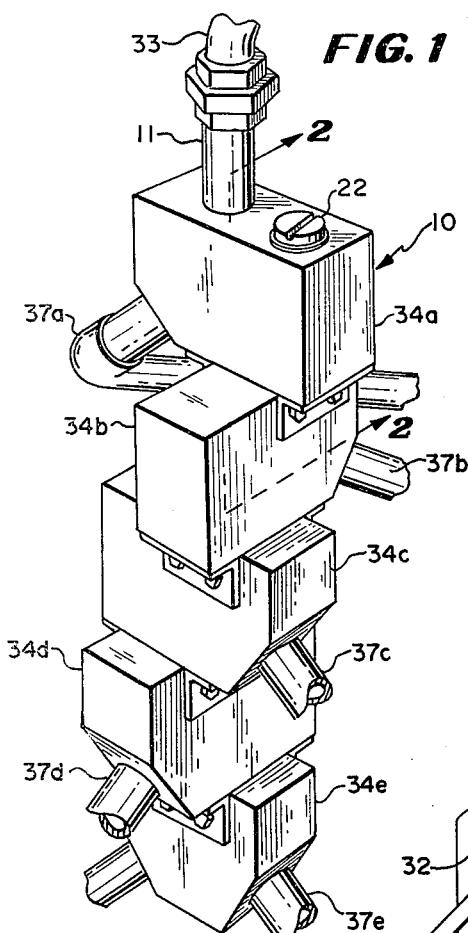
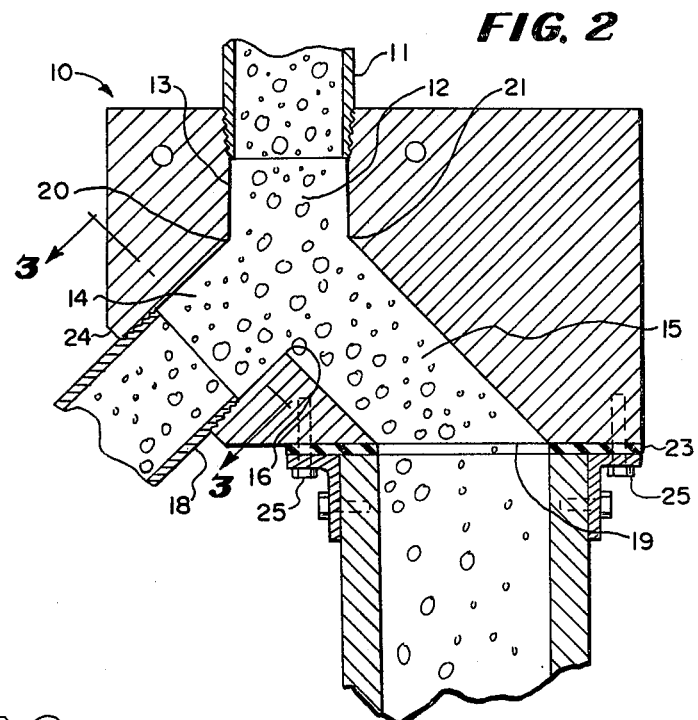
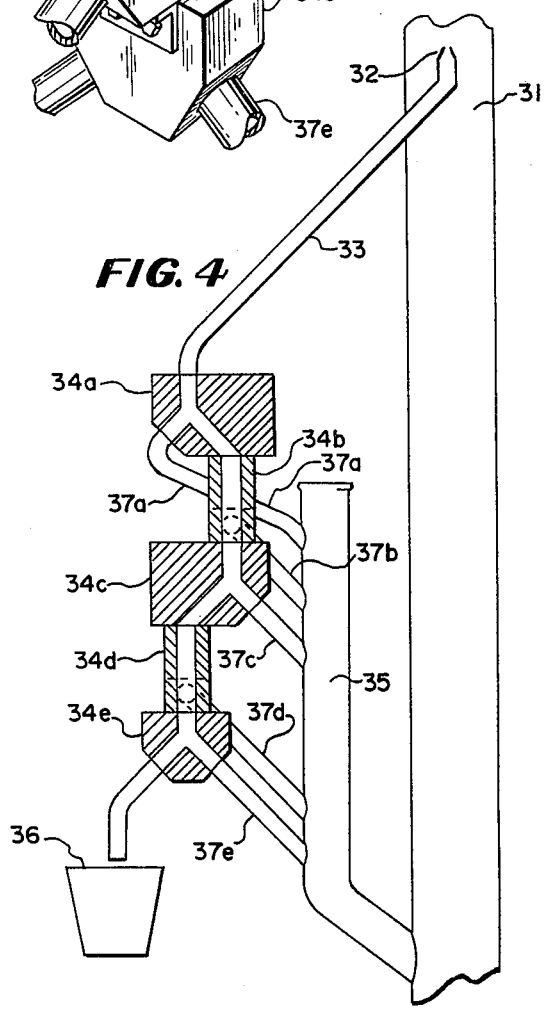
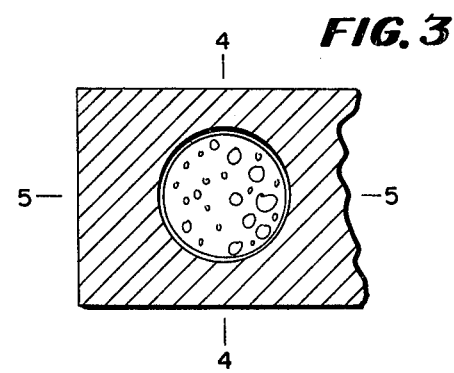

SECONDARY SAMPLING DEVICE

BACKGROUND OF THE INVENTION

This invention generally relates to a sampling device. More particularly, the invention relates to a secondary sampling device for particulate matter.

Many industries process large quantities of raw materials or products in particulate form. Frequently, the quality or value of such material is determined by a physical or chemical analysis of a very small sample. For instance, it is not uncommon to base the quality of a large quantity, such as a railroad car full, of such material on the analysis of a few hundred grams or less of the material. Obviously, very small errors in the analysis can have profound effects on decisions regarding the value or acceptability of the material. A critical step in providing an accurate analysis of such material is to obtain a representative sample.

A sample is usually taken from a feed stream of material in free fall as it passes through a relatively large pipe or chute. Since particulate matter may segregate as it passes through a pipe or chute, for instance, because of differences in particle size or particle density, it is advantageous to obtain a representative sample across the entire cross-section of the sample stream. Obtaining such a sample is the function of a primary sampling device.

Primary sampling devices are commercially available in a variety of designs. They usually include a sample cutter which continuously moves across the product stream at a uniform speed, thereby collecting a representative portion of the entire stream. Although the primary sampler may take only a small portion of the product stream, the amount taken may, nevertheless, be too large for an analysis. In such case, a representative sample must be taken from the material collected by the primary sampler. The equipment used to take such a sample is generally referred to as the secondary sampler.

Secondary samplers are also available in a variety of designs. Generally, secondary samplers, like primary samplers, comprise a moving sample cutter which moves through the product stream from the primary sampler. Although many of such samplers are very effective in obtaining good representative samples, they are usually comprised of motors, gears and other moving parts which increase costs and maintenance expenses.

SUMMARY OF THE INVENTION

Accordingly, it is an object of this invention to provide a sampling device. It is another object of the invention to provide a secondary sampling device for particulate matter. Yet another object is to provide a secondary sampling device for particulate matter which is capable of obtaining relatively small representative samples and which contains no moving parts.

In accordance with the invention, there is disclosed a secondary sampling device for particulate matter, comprising a plurality of sample splitters arranged in series including a top sample splitter and a bottom sample splitter, each sample splitter, including:

a substantially vertical inlet duct having a substantially vertical axis,
an inlet in an upper portion of said duct providing an opening to said substantially vertical inlet duct,
a first outlet duct and a second outlet duct below said inlet having substantially equal cross-sectional areas and both communicating with the inlet duct,
wherein the center axes of the inlet duct and the outlet ducts are in the same plane and intersect at the same point and the angle between the inlet duct and the first outlet duct is substantially equal to the angle between the inlet duct and the second outlet duct and is greater than about one hundred degrees,
a separating edge formed by the intersection of the two outlet ducts, and
a first outlet and a second outlet providing openings for the first outlet duct and second outlet respectively wherein particulate matter enters the secondary sampling device through the inlet of the top sample splitter, the inlet of each subsequent sample splitter joins the first outlet of the preceding sample splitter, and sample is withdrawn from the first outlet of the bottom sample splitter, and the plane of the axes of the inlet and outlet ducts of each sample splitter is substantially vertical and is substantially perpendicular to the same planes of adjacent sample splitters.

BRIEF DESCRIPTION OF THE DRAWINGS

Other objects and advantages of the invention will become apparent to those skilled in the art from the disclosure herein and upon reference to the drawings, in which:

FIG. 1 is a perspective view of a secondary sampling device embodying the principles of the present invention.

FIG. 2 is a partial sectional view of the secondary sampling device taken along line 2—2 of FIG. 1, illustrating a sample splitter which is an element of the present invention.

FIG. 3 is a cross-sectional view of the sample splitter illustrated in FIG. 2 taken along line 3—3 of FIG. 2.

FIG. 4 is a schematic view of a secondary sampling device illustrating its internal structure and its cooperation with a primary sampling device.

While the invention will be described in connection with a preferred embodiment, it will be understood that it is not intended to be limited to that embodiment. On the contrary, it is intended to cover all alternatives, modifications and equivalents as may be included within the spirit and scope of the invention as defined by the appended claim.

DETAILED DESCRIPTION OF THE INVENTION

FIG. 1 illustrates a secondary sampling device embodying the principles of this invention. The device includes a series of sample splitters, 34a, 34b, 34c, 34d, and 34e. The top sample splitter, 34a, is further illustrated in FIG. 2 which is a partial sectional view of the device of FIG. 1.

The sample splitter comprises an inlet 11 providing an opening to substantially vertical inlet duct 13. The inlet duct diverges to form a first outlet duct 14 and a second outlet duct 15 which terminate at first outlet 18 and second outlet 19 respectively. The intersection of the first outlet duct and the second outlet duct forms separating edge 16. In operation, particulate matter 12 enters the secondary sampling device in a continuous stream through inlet 11. The particulate matter splits into two substantially equal streams at separating edge 16 and passes out of the sample splitter through the outlet ducts 14 and 15 and outlets 18 and 19.

To obtain an even sample split, it is important that inlet duct 13 be substantially vertical, thereby avoiding gravitational bias of the particulate matter toward one outlet duct or the other. To aid in maintaining the device in a vertical position, a leveling indicator 22 as shown in FIG. 1, may be affixed to any convenient horizontal surface of the device. A gasket of resilient material 23 between adjacent sample splitters, as shown in FIG. 2, insures a leak-proof connection and also provides that each sample splitter is substantially vertical, through proper torquing of fastening screws 25.

A sample splitter may conveniently be made by boring inlet and outlet ducts into a block 10 of a suitable material, e.g. steel, aluminum, plastic, etc. Accordingly, the cross-sectional shapes of the various ducts are advantageously circular; however, such shape is not critical, and any suitable shape, such as rectangular or oval may be employed. The cross-sectional shapes and areas of the two outlet ducts should be substantially equal to insure equal distribution of the particulate matter to the two ducts. The inlet duct may, advantageously, have a somewhat larger cross-sectional area than that of an outlet duct.

As indicated in FIGS. 1 and 2, inlets and outlets may be in the form of pipes or conduits threaded into the sample splitter ducts. In this regard, the sample splitter may utilize a structure 24 wherein a corner of the sample splitter block is cut off square to the outlet duct 14 through which sample is rejected, to facilitate threading of that outlet duct.

The center axes of the inlet duct and the outlet ducts are in substantially the same plane and intersect at the same point. Furthermore, the angle 20 between the inlet duct and the first outlet duct is substantially equal to the angle 21 between the inlet duct and the second outlet duct. The outlet ducts should slope downward to allow free flow of the particulate matter, therefore, the angle between the inlet duct and an outlet duct is advantageously oblique, preferably greater than about 100° and, most preferably, greater than about 120°.

As particulate matter flows through a sample splitter, one-half of the stream flows through first outlet 18 and one-half through second outlet 19. Therefore, if the material from the second outlet is retained and the material from the first outlet is rejected, e.g. returned to the main product stream, the size of the sample will be reduced by one-half.

To further reduce the sample size, as is frequently desired, a plurality of sample splitters are arranged in series. The sample is reduced by a factor of one-half for each splitter employed. Thus, for a series of five splitters, as shown in FIGS. 1 and 3, the final sample size is 1/32 of that received from the primary sampler.

A problem encountered with arranging a plurality of sample splitters in series is that segregation of the particulate matter may be encountered. This segregation exists when adjacent sample splitters are not in planes perpendicular to each other. The reason for the segregation is illustrated by FIGS. 2 and 3. As particulate matter 12 enters the outlet ducts from the inlet duct, the direction of flow is altered. The heavier particles therefore tend to congregate toward the inner walls of the outlet ducts, whereas the lighter particles tend to be thrown out against the outer walls. The resulting segregation is shown in FIG. 3 which is a cross-sectional view of a sample splitter taken along line 3—3 of FIG. 2. The view shows a majority of the heavier particles in one-half of the section and a majority of the lighter particles in the other half. It can be seen, therefore, that if the effluent from the outlet of the sample splitter were passed through a second sample splitter and were split across line 4—4 of FIG. 2, a majority of the heavier particles would be discharged through one outlet of the second sample splitter and a majority of the lighter particles would be discharged through the other outlet, thus resulting in non-representative sampling.

It has been found, however, that by splitting the sample at a 90° angle to the previous sample split, i.e. along line 5—5 of FIG. 2, a representative sample is obtained. This objective is achieved by the configuration shown in FIGS. 1 and 4.

FIG. 4 is a schematic diagram of the secondary sampling device shown in FIG. 1. A primary sample is taken from a main feed pipe 31 by primary sampler 32. The primary sample is conducted to the secondary sampling device by conduit 33. The primary sample first enters the inlet of sample splitter 34a, where it is divided into halves. The half from the second outlet of sample splitter 34a passes into the inlet of sample splitter 34b. The plane of the axes of the inlet and outlet ducts of sample splitter 34b is substantially perpendicular to the same plane of sample splitter 34a, thus preventing sample segregation as discussed above. The sample continues to pass through successive sample splitters 34c, 34d, and 34e with each sample splitter in a plane perpendicular to those of adjacent sample splitters. The final sample cut which is discharged from the first outlet of sample splitter 34e is collected in an appropriate container 36.

The rejected material, which is discharged from the second outlets of each sample splitter is conducted to a manifold 35 through conduits 37a, 37b, 37c, 37d, and 37e. The rejected material may then be disposed of in any appropriate manner, e.g. returned to the main product stream.

Thus, it is apparent that there has been provided, in accordance with the invention, a secondary sampling device that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations as fall within the spirit and broad scope of the appended claims.

We claim:

1. A secondary sampling device for particulate matter, comprising a plurality of sample splitters arranged in series including a top sample splitter and a bottom sample splitter, each sample splitter, including:

a substantially vertical inlet duct having a substantially vertical axis, an inlet in an upper portion of said duct providing an opening to said substantially vertical inlet duct, a first outlet duct and a second outlet duct below said inlet having substantially equal cross-sectional areas and both communicating with the inlet duct, wherein the center axes of the inlet duct and the outlet ducts are in the same plane and intersect at the same point and the angle between the inlet duct and the first outlet duct is substantially equal to the angle between the inlet duct and the second outlet duct and is greater than about one hundred degrees,
a separating edge formed by the intersection of the two outlet ducts, and
a first outlet and a second outlet providing openings for the first outlet duct and second outlet respectively wherein particulate matter enters the secondary sampling device through the inlet of the top sample splitter, the inlet of each subsequent sample splitter joins the first outlet of the preceding sample splitter, and sample is withdrawn from the first outlet of the bottom sample splitter, and the plane of the axes of the inlet and outlet ducts of each sample splitter is substantially vertical and is substantially perpendicular to the same planes of adjacent sample splitters.

2. The secondary sampling device of claim 1 wherein the angle between the inlet duct and an outlet duct is greater than about 120°.